United States Patent
Rubinstein et al.

(10) Patent No.: US 6,907,130 B1
(45) Date of Patent: Jun. 14, 2005

(54) SPEECH PROCESSING SYSTEM AND METHOD USING PSEUDOSPONTANEOUS STIMULATION

(75) Inventors: Jay Rubinstein, Solon, IA (US); Blake Wilson, Durham, NC (US)

(73) Assignees: University of Iowa Research Foundation, Iowa City, IA (US); Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 09/023,279

(22) Filed: Feb. 13, 1998

(51) Int. Cl.[7] ............................................. H04R 25/00
(52) U.S. Cl. .......................... 381/312; 607/55; 607/56; 607/57; 623/10; 600/25; 381/326; 381/331; 381/151
(58) Field of Search ............................ 607/55–57, 137; 600/25; 381/326, 331, 151, 312, 320, 316, FOR 130; 623/10; 455/40, 41, 43

(56) References Cited

U.S. PATENT DOCUMENTS

| | | | |
|---|---|---|---|
| 3,563,246 A | | 2/1971 | Puharich et al. ............. 128/422 |
| 3,881,495 A | | 5/1975 | Pannozzo et al. ............ 128/422 |
| 4,063,048 A | * | 12/1977 | Kissiah, Jr. ................... 607/57 |
| 4,357,497 A | * | 11/1982 | Hochmair |
| 4,510,936 A | | 4/1985 | Fourcin et al. .............. 128/419 |
| 4,515,158 A | | 5/1985 | Patrick et al. ............... 128/419 |
| 4,577,641 A | | 3/1986 | Hochmair et al. ........... 128/746 |
| 4,593,696 A | | 6/1986 | Hochmair et al. ........... 128/419 |
| 4,611,596 A | | 9/1986 | Wasserman ................. 128/419 |
| 4,648,403 A | | 3/1987 | Van Compernolle ........ 128/419 |
| RE32,947 E | * | 6/1989 | Dormer |
| 4,932,405 A | * | 6/1990 | Peeters et al. ................. 607/57 |
| 4,982,434 A | | 1/1991 | Lenhardt et al. ............ 381/68.3 |

(Continued)

FOREIGN PATENT DOCUMENTS

| | | |
|---|---|---|
| GB | 2 171 605 A | 9/1986 |
| WO | WO9612383 | 4/1996 |

OTHER PUBLICATIONS

Ifukube et al., "Design Of An Implantable Tinnitus Suppressor By Electrical Cochlear Stimulation", Biomechanics, Rehabilitation, Electrical Phenomena, Biomaterials, San Diego, Oct. 28–31, 1993, vol. 3, No. CONF. 15, pp. 1349–1350.

Cohen, N.L. et al., "A Prospective, Randomized Study of Cochlear Implants," N. Engl. J. Med., 328:233–7, 1993.

C.W. Parkins et al., "A Fiber Sum Modulation Code for a Cochlear Prosthesis" Annals of the New York Academy of Sciences, Jan. 1, 1983, vol. 405, pp. 490–501.

P.C. Loizou, "Signal Processing for Cochlear Prosthesis: A Tutorial Review", Proceedings of the 40th Midwest Symposium on Circuits and Systems MWSCAS, IEEE 1997, pp. 881–885.

*Primary Examiner*—Curtis Kuntz
*Assistant Examiner*—Dionne Harvey
(74) *Attorney, Agent, or Firm*—Fleshner & Kim, LLP

(57) ABSTRACT

A apparatus and method for inner ear implants is provided that generates signal processing stochastic independence activity across the excited neural population. A high rate pulse train can produce random spike patterns in auditory nerve fibers (hereafter "pseudospontaneous activity") that are statistically similar to those produced by spontaneous activity in the normal auditory nerve. We call this activity "pseudospontaneous". Varying rates of pseudospontaneous activity can be created by varying the intensity of a fixed amplitude, high rate pulse train stimulus, e.g., 5000 pps. The high rate pulse train can desynchronize the nerve fiber population and can be combined with a data signal in an inner ear implant. The pseudospontaneous activity can enhance neural representation of temporal detail and dynamic range with an inner ear implant such as a cochlear implant. The pseudospontaneous activity can further eliminate a major difference between acoustic- and electrical-derived hearing percepts.

29 Claims, 13 Drawing Sheets

U.S. PATENT DOCUMENTS

| | | | |
|---|---|---|---|
| 5,061,282 A | 10/1991 | Jacobs | 623/10 |
| 5,095,904 A | 3/1992 | Seligman et al. | 128/420.6 |
| 5,215,085 A | 6/1993 | von Wallenberg-Pachaly | 128/420.6 |
| 5,271,397 A * | 12/1993 | Seligman et al. | 607/137 |
| 5,549,658 A | 8/1996 | Shannon et al. | 607/57 |
| 5,571,148 A * | 11/1996 | Loeb | |
| 5,597,380 A | 1/1997 | McDermott et al. | 607/57 |
| 5,601,617 A | 2/1997 | Loeb et al. | 607/56 |
| 5,649,970 A | 7/1997 | Loeb et al. | 607/57 |
| 5,735,885 A | 4/1998 | Howard, III et al. | 607/55 |
| 6,169,813 B1 * | 1/2001 | Richardson | |
| 6,217,508 B1 * | 4/2001 | Ball | |
| 6,249,704 B1 | 6/2001 | Maltan et al. | 607/57 |

* cited by examiner

SPEECH PROCESSING SYSTEM AND METHOD USING PSEUDOSPONTANEOUS STIMULATION

Part of the work performed during the development of this invention utilized U.S. Government funds under grant DC 6211 and contract OD 02948 from the National Institute of Health. The government may have certain rights in this invention.

BACKGROUND OF THE INVENTION

1. Field of the Invention

This invention relates generally to an system and method for providing pseudospontaneous neural stimulation. In particular, the invention relates to an apparatus and method for providing pseudospontaneous activity in the auditory nerve, which can be used to treat a sensorineural deafness patient. Electrical signals that induce pseudospontaneous neural activity in the auditory nerve can be delivered to the patient via an inner ear (cochlear) implant.

2. Background of the Related Art

At least two distinct types of hearing problems are recognized: conductive hearing loss and sensorineural hearing loss. The former is generally due to a mechanical defect in the middle ear that prevents sound-related vibrations from reaching the inner ear. In the latter, sound-related vibrations reach the inner ear, but signal transmission to the brain does not occur or is restricted. Sensorineural hearing loss usually results from damage to the cochlea and/or the auditory nerve. Sensorineural hearing loss is a common condition that may occur in old age, or may be due to exposure to excessively loud noises (e.g. rock concerts, jet engines), viral infections, etc.

Patients experiencing a certain amount of hearing loss may benefit from the use of a hearing aid which increases the volume of sound electronically, and which may be placed either behind the pinna of the ear or within the outer ear canal. In both cases, the device usually comprises a microphone for transforming sound waves into electrical signals, an amplifier for increasing the strength of the electrical signals, and an earphone for providing amplified sounds. Devices designed to treat deafness must obviously consider the underlying cause of deafness. For example, a sensorineural deafness patient with a defective cochlea who still has a functional auditory nerve, may benefit from a cochlear implant, as described hereinbelow. However, if the auditory nerve is itself damaged and cannot carry electrical signals, then the problem is "too far downstream" in the signal processing sequence for a cochlear implant to be effective. In that situation, artificial signals must enter the auditory system "beyond the block" for example, in the brain stem or in the auditory cortex.

Cochlear implants were designed for patients who are deaf as a result of loss of the cochlea's sound transduction mechanism. In this situation, an electrode is implanted in the cochlea whereby the electrode, upon receiving electrical signals from a speech processor directly stimulates the auditory nerve. Consequently, candidates for a cochlear implant device must have an intact auditory nerve capable of carrying electrical signals to the brain stem. The cochlear implant device delivers electrical signals e.g., by means of a multi-contact stimulating electrode. The stimulating electrode is surgically inserted by an otolaryngologist into the damaged cochlea. Activation of the contacts stimulates auditory nerve terminals that are normally activated by the cochlear sound transduction mechanism (hair cells-spiral ganglion). The patient perceives sound as the coded electrical signal carried into the brain by the auditory nerve. (See for example, Cohen, N. L. et al., "A Prospective, Randomized Study of Cochlear Implants," *N. Engl. J. Med.*, 328:233–7, 1993.)

Cochlear implants are surgically placed in the cochlea within the temporal bone with little risk to the patient, because patients who are already deaf due to a defective cochlea have little chance of any additional injury being caused by placement of a cochlear implant. In patients with hearing loss caused by dysfunction at the level of the cochlea, cochlear implants can restore hearing.

However, fundamental differences currently exist between electrical stimulation and acoustic stimulation of the auditory nerve. Electrical stimulation of the auditory nerve, for example, via a cochlear implant, generally results in more cross-fiber synchrony, less within fiber jitter, and less dynamic range, as compared with acoustic stimulation which occurs in individuals having normal hearing. As a result, hearing percepts experienced by sensorineural deafness patients via a cochlear implant lack the coherence and clarity characteristics of normal hearing.

FIG. 15 shows a related art pattern of electrically-evoked compound action potentials (EAPs) magnitudes from an auditory nerve of a human subject with an electrical stimulus of 1 kHz (1016 pulses/s). The EAP magnitudes are normalized to the magnitude of the first EAP in the record. FIG. 15 shows the typical alternating pattern previously described in the art. This pattern arises because of the refractory period of the nerve and can degrade the neural representation of the stimulus envelope. With a first stimulus 1502, a large response occurs likely because of synchronous activation of a large number of nerve fibers. These fibers are subsequently refractory during a second pulse 1504, and accordingly, a small response is generated. By the time of a third pulse 1506, an increased pool of fibers becomes available and the corresponding response increases. The alternating synchronized response pattern can be caused by a lack or decrease of spontaneous activity in the auditory nerve and can continue indefinitely.

The above reference is incorporated by reference herein where appropriate for appropriate teachings of additional or alternative details, features and/or technical background.

SUMMARY OF THE INVENTION

An object of the present invention is to provide an apparatus and method for neural stimulation that substantially obviates at least the problems and disadvantages of the related art.

Another object of the present invention is to provide an apparatus and method that generates stochastically independent or pseudospontaneous neural activity.

A further object of the present invention is to provide an apparatus and method that generates pseudospontaneous activity in an auditory nerve to improve response to signals representing sound.

A further object of the present invention is to provide an apparatus and method that combines a conditioner signal and a data signal and provides the combined signals to a neural system to improve the response of the neural system to the data signal.

A further object of the present invention is to provide a cochlear implant, and method for using same, that provides a conditioner and a data signal to improve speech communications in a sensorineural deafness patient via a cochlear implant.

To achieve at least the above objects in whole or in part, there is provided a cochlear implant system according to the present invention that includes a first signal that represents sound, a signal generator that generates a second signal causing pseudospontaneous activity, a signal processor that combines a first signal and the second signal to output combined signals, and a stimulation unit coupled to the signal processor that receives the combined signal from the signal processor.

To further achieve at least the above objects in a whole or in parts, there is provided a method for generating a driving signal for an auditory implant according to the present invention that includes receiving a first signal, generating a second signal that causes pseudospontaneous activity in an auditory nerve and combining the first and second signals to generate the driving signal.

To further achieve at least the above objects in a whole or in parts, there is provided an auditory prosthesis according to the present invention for receiving an auditory signal representing sound and supplying an electrical signal that is adapted to stimulate the auditory nerve of a person that includes a pseudospontaneous generation device that generates a pseudospontaneous driving signal, a transducer device adapted to receive the auditory signal and the pseudospontaneous driving signal that transforms the signal to an electrical input signal, a generation unit operatively coupled to the electrical input signal that generates a plurality of electrical signals selectively replicating the temporal nerve discharge pattern of individually located auditory nerve fibers within the cochlea of a person and a stimulation device, operatively coupled to the plurality of electrical signals of the generation unit, that stimulates selected auditory nerve sites within the cochlea.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The auditory system is composed of many structural components, some of which are connected extensively by bundles of nerve fibers. The auditory system enables humans to extract usable information from sounds in the environment. By transducing acoustic signals into electrical signals, which are processed in the brain, humans can discriminate among a wide range of sounds with great precision.

Figure 1:
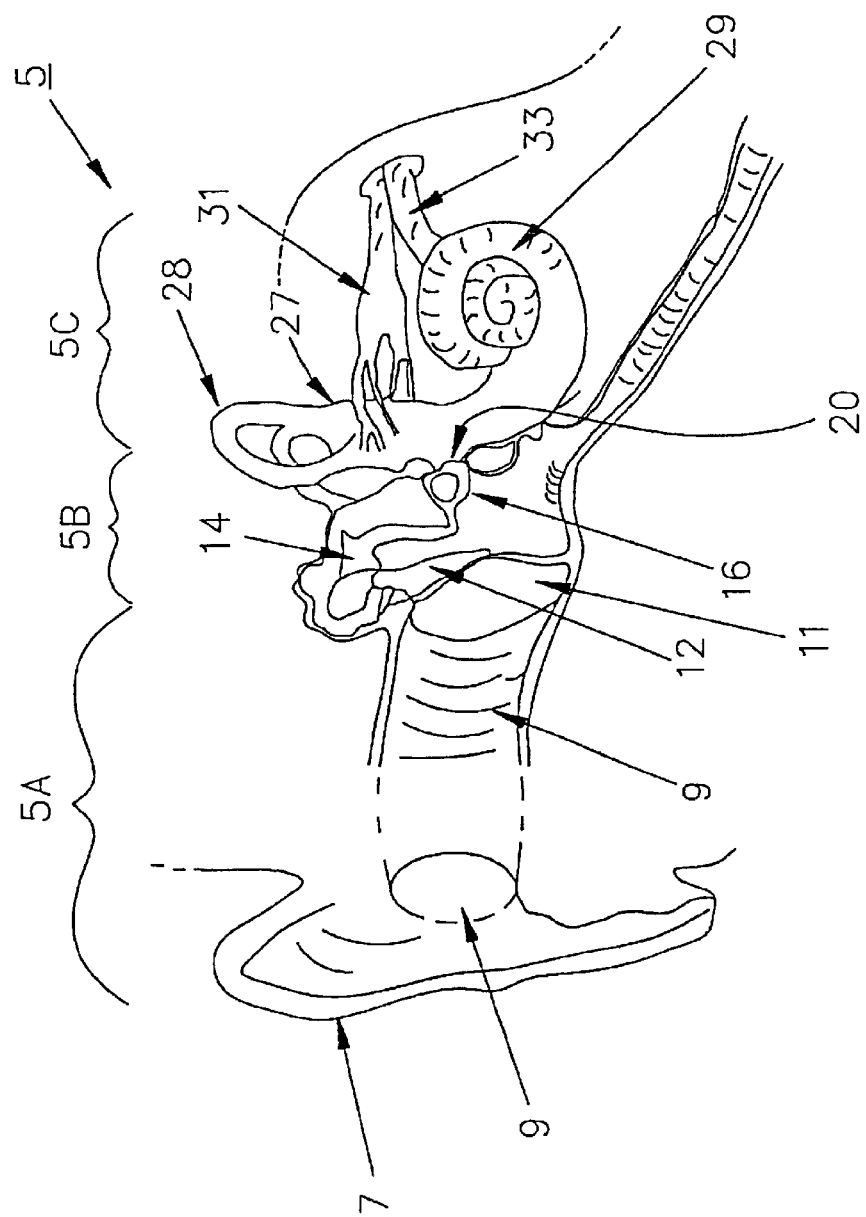
FIG. 1 is a diagram showing section view of the human ear as seen from the front.

FIG. 1 shows a sectional view of a human ear 5, which includes the outer ear 5A, middle ear 5B and inner ear 5C. The outer ear 5A includes pinna 7 having folds of skin and cartilage and outer ear canal 9, which leads from the pinna 7 at its proximal end to the eardrum 11 at its distal end. The eardrum 11 includes a membrane extending across the distal end of the outer ear canal 9. The middle ear 5B is located between the eardrum 11 and the inner ear 5C and includes three small connected bones (ossicles), namely the hammer 12, the anvil 14, and the stirrup 16. The hammer 12 is connected to the inner portion of the eardrum 11, the stirrup 16 is attached to oval window 20, and the anvil 14 is located between and attached to each of the hammer 12 and the stirrup 16. A round or oval window 20 leads to the inner ear 5C. The inner ear 5C includes the labyrinth 27 and the cochlea 29, each of which is a fluid-filled chamber. The labyrinth 27, which is involved in balance, includes the semicircular canals 28. Vestibular nerve 31 attaches to the labyrinth 27. Cochlea 29 extends from the inner side of the round window 20 in a generally spiral configuration, and plays a key role in hearing by transducing vibrations transmitted from middle ear 5B into electrical signals for transmission along auditory nerve 33 to the hearing centers of the brain (FIGS. 2A and 2B).

In normal hearing, sound waves collected by the pinna 7 are funneled down the outer ear canal 9 and vibrate the eardrum 11. The vibration is passed to the ossicles (hammer 12, anvil 14, and stirrup 16). Vibrations pass through the round window 20 via the stirrup 16 causing the fluid within the cochlea 29 to vibrate. The cochlea 29 is equipped internally with a plurality of hair cells (not shown). Neurotransmitters released by the hair cells stimulate the auditory nerve 33 thereby initiating signal transmission along the auditory nerve 33. In normal hearing, the inner hair cell-spiral ganglion is inherently "noisy" in the absence of sound because of the random release of neurotransmitters from hair cells. Accordingly, in normal hearing, spontaneous activity in the auditory nerve occurs in the absence of sound.

Figure 2B:
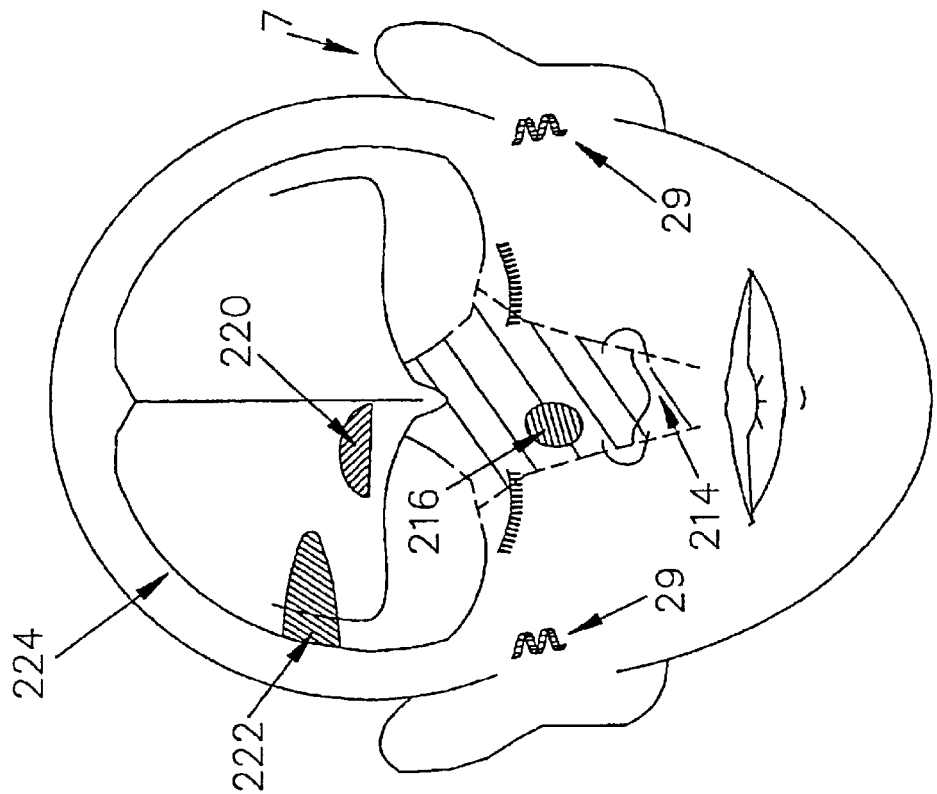
FIGS. 2A and 2B are diagrams showing the relative positions of the hearing elements including the external ear, auditory cortex, cochlea and cochlear nucleus.
Figure 2A:
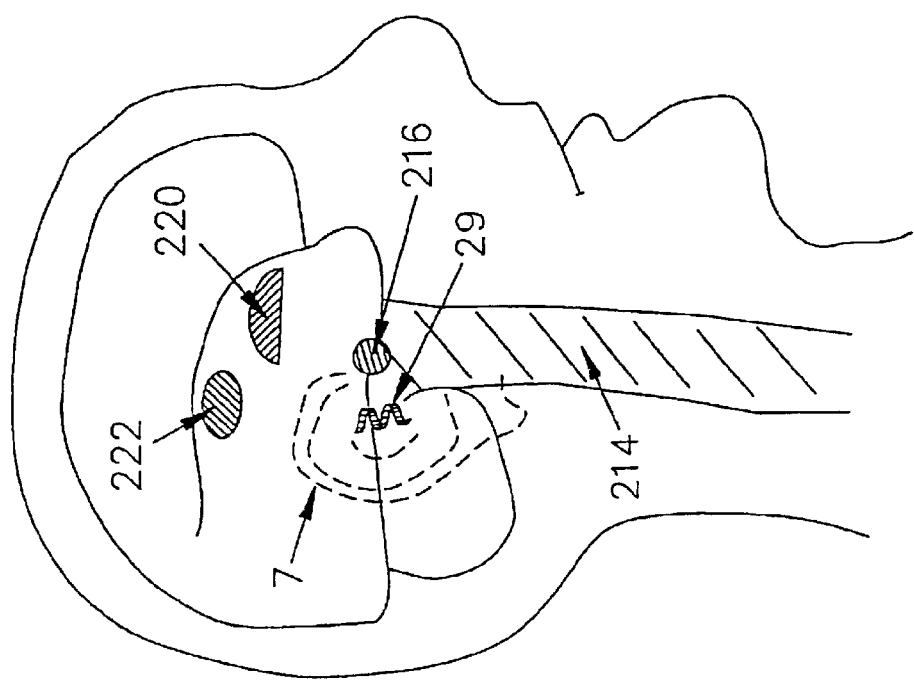

FIGS. 2A and 2B respectively show a side view and a front view of areas involved in the hearing process, including the pinna 7 and the cochlea 29. In particular, the normal transduction of sound waves into electrical signals occurs in the cochlea 29 that is located within the temporal bone (not shown). The cochlea 29 is tonotopically organized, meaning different parts of the cochlea 29 respond optimally to different tones; one end of the cochlea 29 responds best to high frequency tones, while the other end responds best to low frequency tones. The cochlea 29 converts the tones to electrical signals that are then received by the cochlea nucleus 216, which is an important auditory structure located in the brain stem 214. As the auditory nerve leaves the temporal bone and enters the skull cavity, it penetrates the brain stem 214 and relays coded signals to the cochlear nucleus 216, which is also tonotopically organized. Through many fiber-tract interconnections and relays (not shown), sound signals are analyzed at sites throughout the brain stem 214 and the thalamus 220. The final signal analysis site is the auditory cortex 222 situated in the temporal lobe 224.

Information is transmitted along neurons (nerve cells) via electrical signals. In particular, sensory neurons such as those of the auditory nerve carry information about sounds in the external environment to the central nervous system (brain). Essentially all cells maintain an electrical potential (i.e., the membrane potential) across their membranes. However, nerve cells use membrane potentials for the purpose of signal transmission between different parts of an organism. In nerve cells, which are at rest (i.e., not transmitting a nerve signal) the membrane potential is referred to as the resting potential (Vm). The electrical properties of the plasma membrane of nerve cells are subject to abrupt change in response to a stimulus (e.g., from an electrical impulse or the presence of neurotransmitter molecules), whereby the resting potential undergoes a transient change called an action potential. The action potential causes electrical signal transmission along the axon (i.e., conductive core) of a nerve cell. Steep gradients of both Na+ and K+ are maintained across the plasma membranes of all cells via the Na—K pump.

TABLE 1

| ION | [INSIDE] (mM) | [OUTSIDE] (mM) |
|---|---|---|
| K+ | 140 | 5 |
| Na+ | 10 | 145 |

Such gradients provide the energy required for both the resting potential and the action potential of neurons. Concentration gradients for Na+ and K+ (in the axon of a mammalian neuron) are shown in Table 1. In a resting neuron, K+ is near electrochemical equilibrium, while a large electrochemical gradient exists for Na+. However, little trans-membrane movement of Na+ occurs because of the relative impermeability of the membrane in the resting state. In the resting state, the voltage-sensitive Na+ specific channels and the voltage-sensitive K+ specific channels are both closed. The passage of a nerve impulse along the axonal membrane is because of a transient change in the permeability of the membrane, first to Na+ and then to K+, which results in a predictable pattern of electrical changes propagated along the membrane in the form of the action potential.

The action potential of a neuron represents a transient depolarization and repolarization of its membrane. As alluded to above, the action potential is initiated by a stimulus, either from a sensory cell (e.g., hair cell of the cochlea) or an electrical impulse (e.g., an electrode of a cochlear implant). Specifically, upon stimulation the membrane becomes locally depolarized because of a rapid influx of Na+ through the voltage-sensitive Na+ channels. Current resulting from Na+ influx triggers depolarization in an adjacent region of the membrane, whereby depolarization is propagated along the axon. Following depolarization, the voltage-sensitive K+ channels open. Hyperpolarization results because of a rapid efflux of K+ ions, after which the membrane returns to its resting state. (See, for example, W. M. Becker & D. W. Deamer, *The World of the Cell*, 2nd Ed., pp. 616–640, Benjamin/Cummings, 1991. (hereafter Becker)) The above sequence of events requires only a few milliseconds.

Figure 3A:
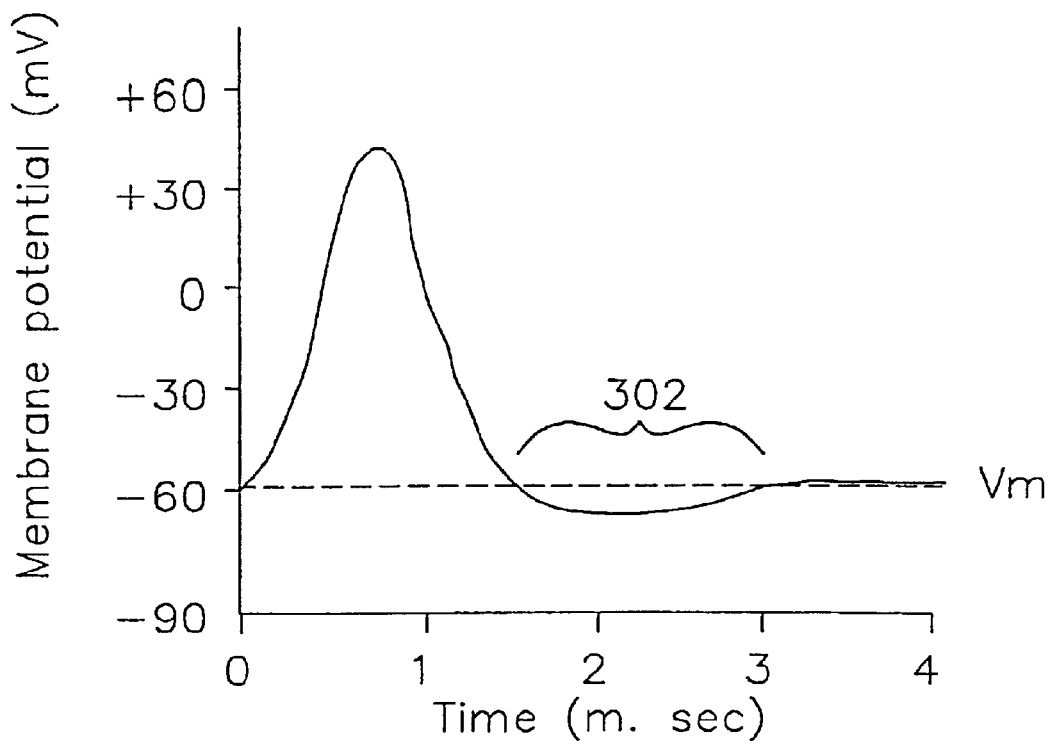
FIG. 3A is a diagram showing neuronal membrane potential during transmission of a nerve impulse.
Figure 3B:
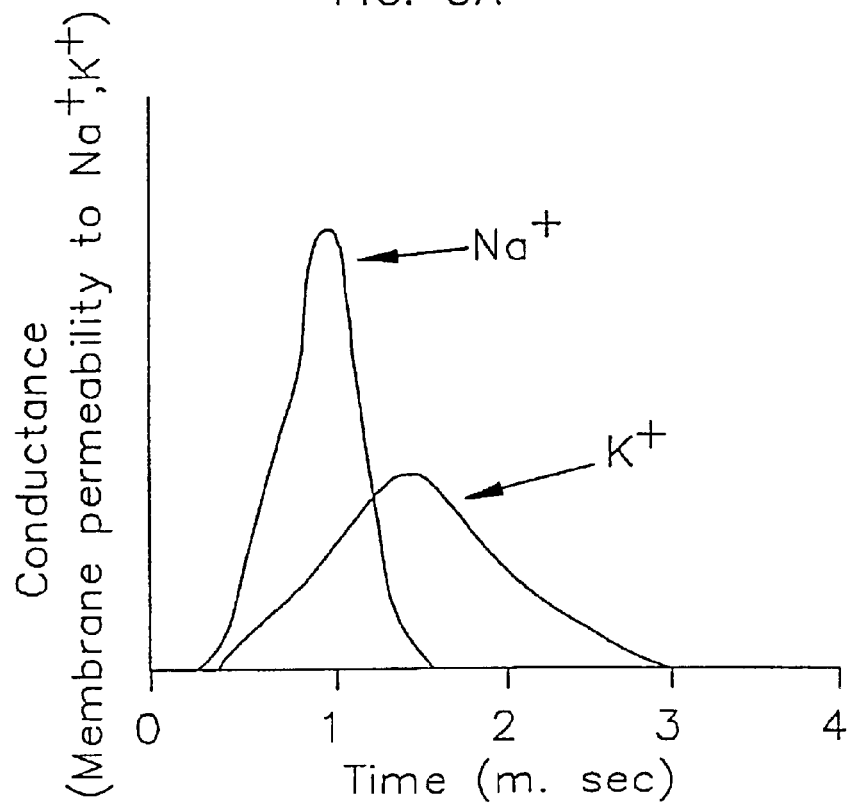
FIG. 3B is a diagram showing the changes in permeability of the plasma membrane to Na+ and K+ during the generation of an action potential.

FIG. 3A shows a membrane potential of a nerve cell during elicitation of an action potential in response to a stimulus. During generation of an action potential, the membrane first becomes depolarized above a threshold level of at least 20 mV such that the membrane is rendered transiently very permeable to Na+, as shown in FIG. 3B, leading to a rapid influx of Na+. As a result, the interior of the membrane becomes positive for an instant and the membrane potential increases rapidly to about +40 mV. This increased membrane potential causes an increase in the permeability of the membrane to K+. A rapid efflux of K+ results and a negative membrane potential is reestablished at a level below the resting potential (Vm). In other words, the membrane becomes hyperpolarized 302 as shown in FIG. 3A. During this period of hyperpolarization 302, the sodium channels are inactivated and unable to respond to a depolarization stimulus. The period 302 during which the sodium channels, and therefore the axon, are unable to respond is called the absolute refractory period. The absolute refractory period ends when the membrane potential returns to the resting potential. At resting potential, the nerve cell can again respond to a depolarizing stimulus by the generation of an action potential. The period for the entire response of a nerve cell to a depolarizing stimulus, including the generation of an action potential and the absolute refractory period, is about 2.5 to about 4 ms. (See, for example, Becker, pp. 614–640)

As alluded to herein above, in a normal cochlea the inner hair cell-spiral ganglion is inherently "noisy" (i.e., there is a high background of activity in the absence of sound) resulting in spontaneous activity in the auditory nerve. Further, sound produces a slowly progressive response within and across fiber synchronization as sound intensity is increased. The absence of spontaneous activity in the auditory nerve can lead to tinnitus as well as other hearing-related problems.

According to the preferred embodiments of the present invention, the artificial induction of a random pattern of activation in the auditory nerve of a tinnitus patient or a hard-of-hearing patient mimics the spontaneous neural activation of the auditory nerve, which routinely occurs in an individual with normal hearing and lacking tinnitus. The artificially induced random pattern of activation of the auditory nerve is hereafter called "Pseudospontaneous". In the case of an individual having a damaged cochlea, such induced pseudospontaneous stimulation activation of the auditory nerve may be achieved, for example, by the delivery of a high rate pulse train directly to the auditory nerve via a cochlea implant. Alternatively, in the case of a patient with a functional cochlea, pseudospontaneous stimulation of the auditory nerve may be induced directly by stimulation via an appropriate middle ear implantable device. Applicant has determined that by inducing pseudospontaneous activity and desynchronizing the auditory nerve, the symptoms of tinnitus may be alleviated.

Preferred embodiments of the present invention emphasize stochastic independence across an excited neural population. A first preferred embodiment of a neural driving signal according to the present invention that generates pseudospontaneous neural activity will now be described. In particular, high rate pulse trains according to the first preferred embodiment can produce random spike patterns in auditory nerve fibers that are statistically similar to those produced by spontaneous activity in the normal spiral ganglion cells. Simulations of a population of auditory nerve fibers illustrate that varying rates of pseudospontaneous activity can be created by varying the intensity of a fixed amplitude, high rate pulse train stimulus. Further, electrically-evoked compound action potentials (EAPs) recorded in a human cochlear implant subject verify that such a stimulus can desynchronize the nerve fiber population. Accordingly, the preferred embodiments according to the present invention can eliminate a major difference between acoustic and electric hearing. An exemplary high rate pulse train driving signal 1102 according to the first embodiment is shown in FIG. 1.

A population of 300 modeled auditory nerve fibers (ANF) has been simulated on a Cray C90 (vector processor) and IBM SP-2 (parallel processors) system., The ANF model used a stochastic representation of each node of Ranvier and a deterministic representation of the internode. Recordings were simulated at the 13th node of Ranvier, which approximately corresponds to the location of the porus of the internal auditory canal assuming the peripheral process has degenerated. Post-stimulus time (PST) histograms and interval histograms were constructed using 10 ms binning of the peak of the action potential. As is well-known in the art, a magnitude of the EAPs is measured by the absolute difference in a negative peak (N1) after pulse onsets and a positive peak (P2) after pulse onsets.

Stimuli presented to the ANF model were a high rate pulse train of 50 $\mu$s monophasic pulses presented at 5 kHz for 18 ms from a point source monopolar electrode located 500 $\mu$m perpendicularly from the peripheral terminals of the axon population. All acoustic nerve fibers were simulated as being in the same geometric location. Thus, each simulation can be considered to represent either 300 fibers undergoing one stimulus presentation or a single fiber undergoing 300 stimulus presentations. In addition, a first stimulus of the pulse train was of sufficient magnitude to evoke a highly synchronous spike in all 300 axons; all subsequent pulses are of an equal, smaller intensity. The first stimulus substantially increased computational efficiency by rendering all fibers refractory with the first pulse of the pulse train.

Two fibers were simulated for eight seconds using the parameters described above. Spike times were determined with one $\mu$s precision and assembled into 0.5 ms bins. Conditional mean histograms, hazard functions and forward recurrence time histograms were calculated (using 0.5 ms bins because of the small number of spikes (1000) simulated) as known to one of ordinary skill in the art. For example, see *Analysis of Discharges Recorded Simultaneously From Pairs of Auditory Nerve Fibers*, D. H. Johnson and N. Y. S. Kiang, Journal of Biophysics, 16, 1976, pages 719–734, (hereafter Johnson and Kiang), hereby incorporated by reference. See also *"Pseudospontaneous Activity: Stochastic Independence of Auditory Nerve Fibers with Electrical Stimulation,"* J. T. Rubinstein, et al., pages 1–18, 1998, hereby incorporated by reference.

Figure 4A:
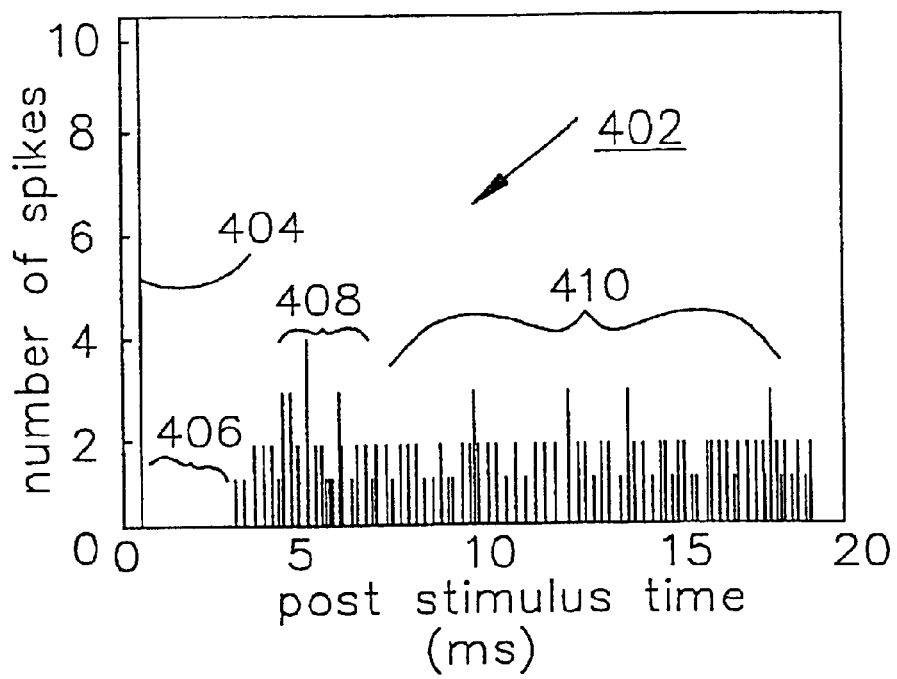
FIGS. 4A and 4B are diagrams showing histograms of modeled responses of the human auditory nerve to a high rate pulse train.

FIG. 4A shows a post-stimulus time (PST) histogram 402 of discharge times from the ANF model with a stimulus amplitude of 325 $\mu$A. A highly synchronous response 404 to a first, higher amplitude pulse was followed by a "dead time" 406. Then, an increased probability of firing 408 was followed by a fairly uniform firing probability 410. The y-axis of the PST histogram has been scaled to demonstrate temporal details following the highly synchronous response to the first pulse. There was a small degree of synchronization with the stimulus as measured by a vector strength of 0.26.

Figure 4B:
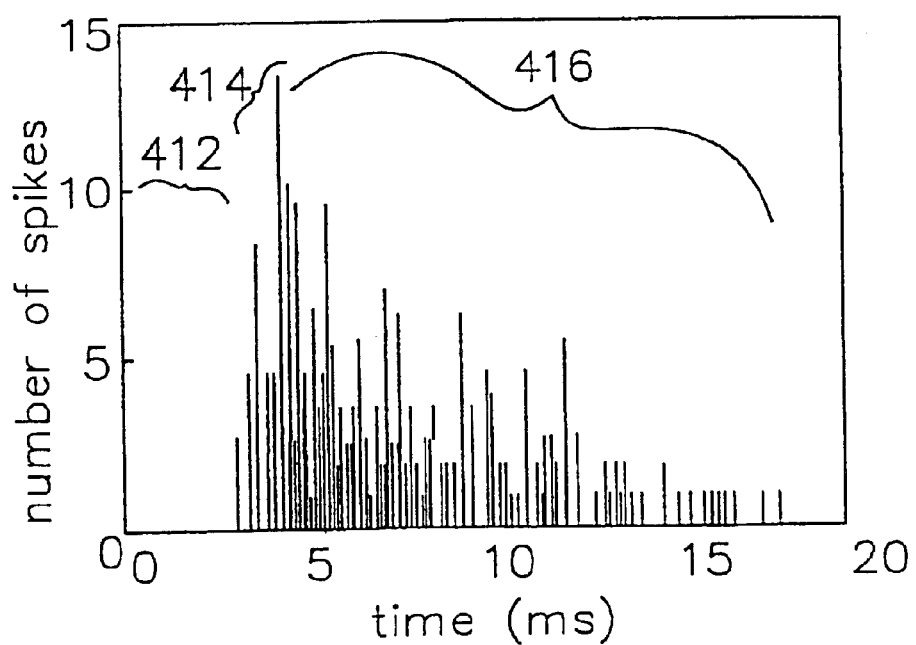
Figure 5B:
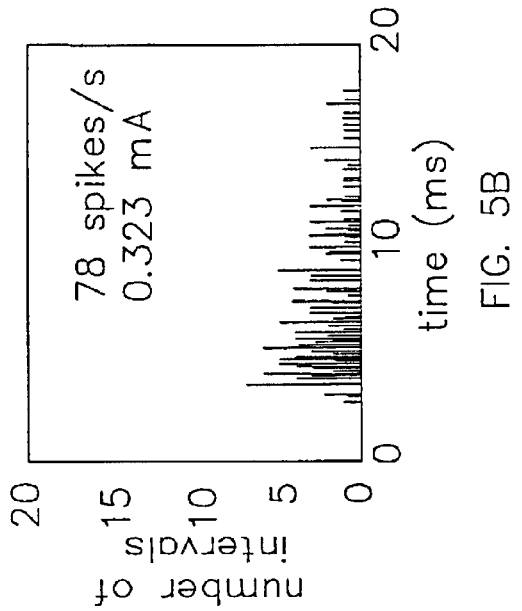
FIGS. 5A–5D are diagrams showing interval histograms of modeled responses of the human auditory nerve to a high rate pulse train at various intensities.
Figure 5D:
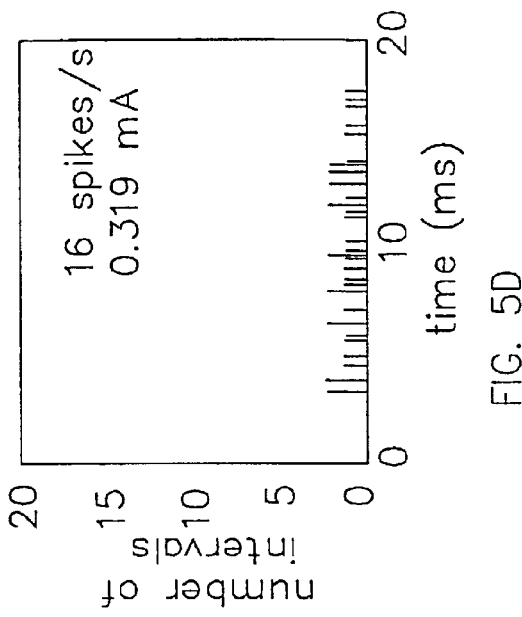
Figure 5A:
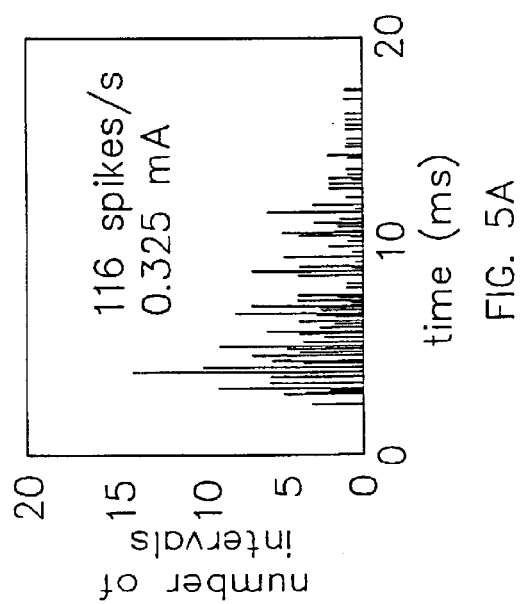
Figure 5C:
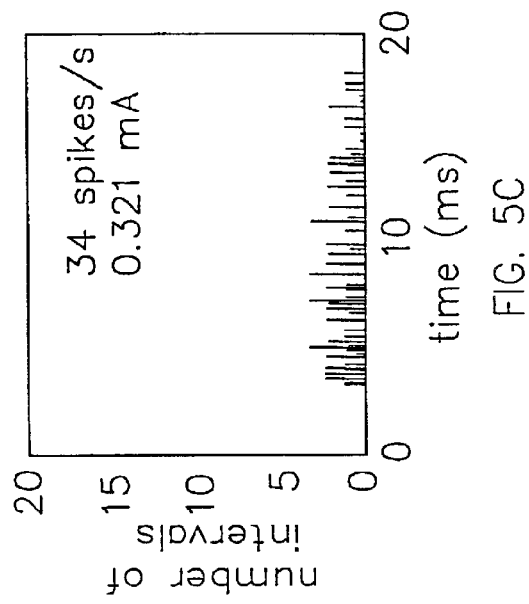

FIG. 4B shows an interval histogram of the same spike train. As shown in FIG. 4B, a dead time 412 was followed by a rapid increase in probability 414 and then an exponential decay 416. The interval histogram is consistent with a Poisson process following a dead time, a renewal process, and greatly resembles interval histograms of spontaneous activity in the intact auditory nerve. These simulation results corresponds to a spontaneous rate of 116 spikes/second measured during the uniform response period of 7 to 17 ms.

As shown in FIGS. 5A–5D, when the stimulus intensity was varied in the ANF model, the firing rate and shape of the PST and interval histograms changed. FIGS. 5A–5D show four interval histograms of a response to a 5 kHz pulse train at different stimulus intensities that demonstrated a range of possible firing rates. The histograms changed shape with changes in pseudospontaneous rate in a manner consistent with normal auditory nerve fibers. All demonstrate Poisson-type intervals following a dead-time. The firing rate during the period of uniform response probability is given in the upper right corner of each plot. Similarly, as respectively shown in FIGS. 8 and 9, a conditional mean histogram and a hazard function for a single "unit" simulated for eight seconds were within standard deviations of theoretical limits. Thus, the conditional mean histogram was "constant," which is consistent with a renewal process, and indicated that a firing probability was not affected by intervals prior to the previous spike. The hazard function was also "constant" after a dead-time, followed by a rapidly rising function. Thus, both plots were consistent with a renewal process much like spontaneous activity, at least for the intervals for which the ANF model had an adequate sample.

Figure 6:
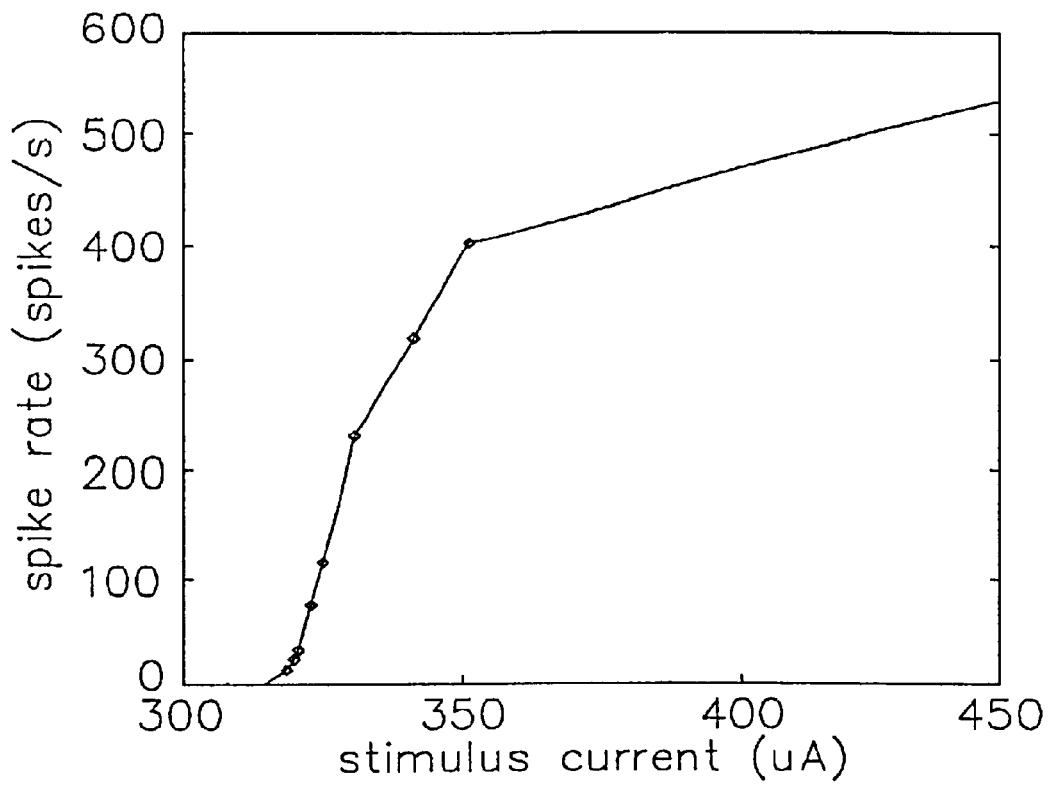
FIG. 6 is a diagram showing a relationship between stimulus intensity and pseudospontaneous rate.

FIG. 6 shows the relationship between stimulus intensity and pseudospontaneous rate. A full range of spontaneous rates, previously known in animal, (from zero to approximately 150 spikes/s), was demonstrated over a relatively narrow range of stimulus intensity for the high rate pulse train stimulation in a computer simulation. Since there is minimal synchronization with the stimulus, compound action potentials in response to individual pulses would be expected to be small or unmeasurable.

Figure 7:
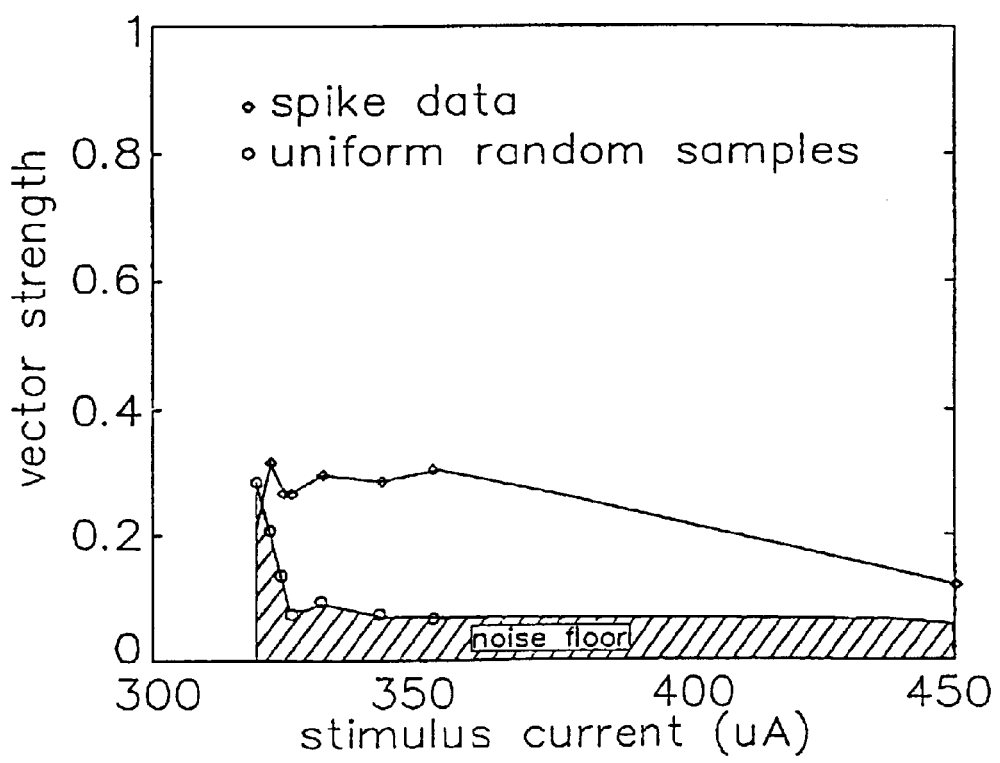
FIG. 7 is a diagram showing a relationship between stimulus intensity and vector strength.

Normal spontaneous activity is independent across neurons. Since pseudospontaneous activity is driven by a common stimulus, one measure of the relative degree of dependence/independence and individual nerve fibers within the auditory nerve was vector strength. Vector strength is a measure of the degree of periodicity or synchrony with the stimulus. Vector strength is calculated from period histograms and varies between 0 (no periodicity) and 1 (perfect periodicity). If vector strength is "high" then each fiber will be tightly correlated with the stimulus and two such fibers will be statistically dependent. If vector strength is "low" then two such fibers should be independent. As shown in FIG. 7, a relationship between stimulus intensity and vector strength is nonzero, but is below or near a noise floor at all intensities tested for the high rate pulse train stimulation. In addition, there is little effect of stimulus amplitude on synchrony. A noise floor for the vector strength calculation was obtained from 500 samples of a set of uniform random numbers whose size is equal to the number of spikes recorded at that stimulus intensity.

Figure 8A:
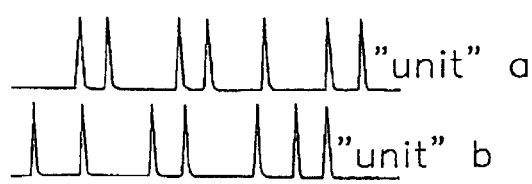
FIG. 8A is a diagram showing two exemplary unit waveforms.
Figure 8B:
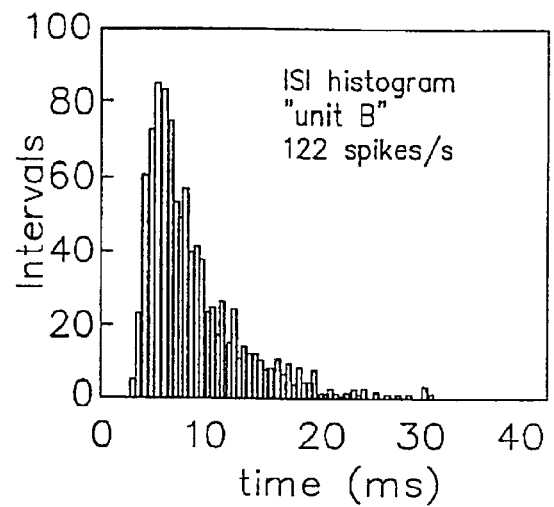
FIG. 8B is a diagram showing an interval histogram.
Figure 8C:
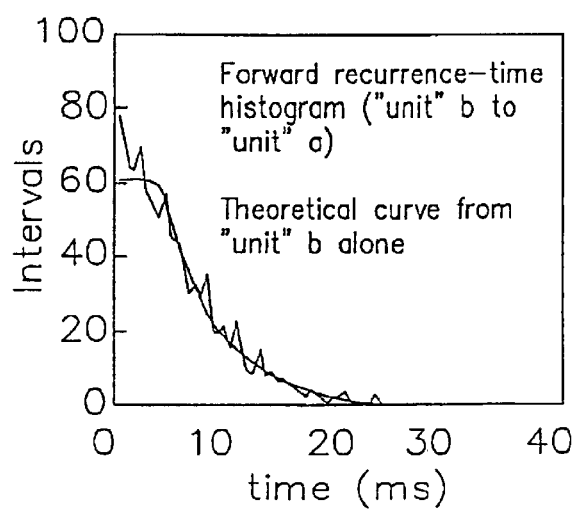
FIGS. 8C–8D are diagrams showing exemplary recurrence time data.
Figure 8D:
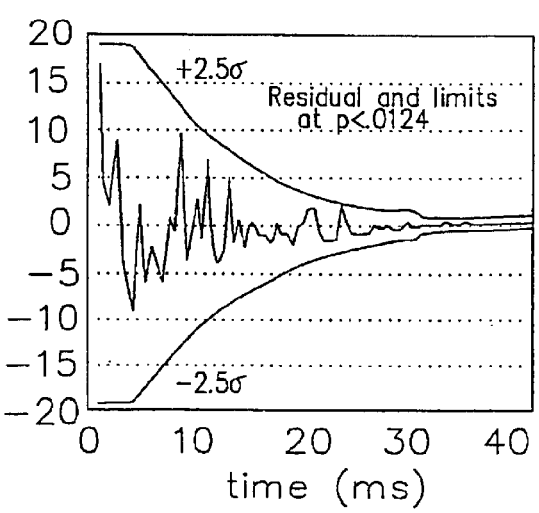

A more rigorous evaluation of fiber independence is a recurrence-time test. (See, for example, Johnson and Kiang.) By using a bin size of 0.5 ms, useful recurrence-time histograms were assembled from two 2-second spike trains of the ANF model simulation. FIG. 8A shows a 50 ms sample of spike activity from two "units" (i.e., two simulated neurons). FIG. 8B shows an ISI histogram from an eight second run of "unit" b. FIG. 8C shows a forward recurrence-time histogram of "unit" b to "unit" a, and a theoretical recurrence-time from "unit" b assuming that "units" a and b are independent. The theoretical forward recurrence-time curve is flat during the refractory period. Theoretical limits are shown at $p<0.0124$ (2.5 standard deviations). FIG. 8D shows residuals calculated by subtracting the curves in FIG. 8C. Thus, the ANF model demonstrated pseudospontaneous activity caused by high rate pulse train stimulation.

Figure 9:
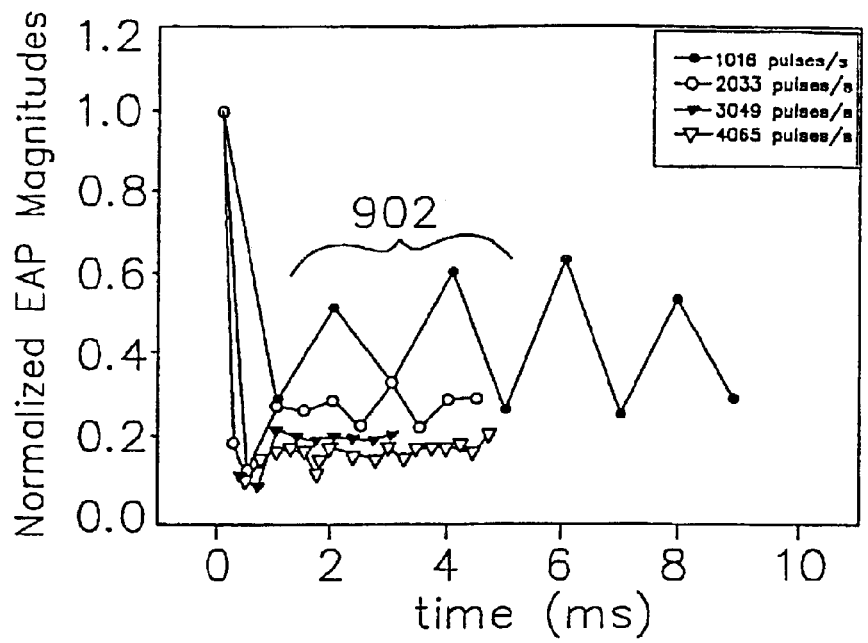
FIG. 9 is a diagram showing magnitudes of EAPs from a human subject with variable rate pulse train.

FIG. 9 shows increases in pulse rates above 1016/s. In particular, FIG. 9 shows magnitudes of electrically-evoked compound action potentials (EAPs) produced with stimulation of human implant subject intracochlear electrodes with identical pulses presented at varied rates. The magnitudes were normalized to the magnitude of the EAP following the first pulse. The pulse amplitude was 375 mA and the pulse duration was 33 $\mu$s/phase. Stimulations were applied using one electrode (i.e., electrode 3) and recordings were made with an adjacent electrode (i.e., electrode 4). Body potential was measured with a reference electrode at the wrist. Methods for generating EAP responses are known in the art. EAP responses in FIG. 9 were determined using a subtraction technique to remove the influence of all prior stimuli and the corresponding responses from the response to a final pulse in a train. In other words, the response to the Nth pulse for each condition was determined by subtracting a record for an N−1 pulse train from a record for an N pulse train, which leaves only the response to the Nth pulse. Without such subtraction, prior EAPs would overlap because the approximately 1 ms duration of an EAP waveform was greater than the interval between sequential pulses and EAPs for pulse rates greater than about 1000/s.

As shown in FIG. 9, the magnitudes of EAPs were produced with stimulation of an intracochlear implant with identical pulses respectively presented at the rates of 1016, 2033, 3049 and 4065/s. Increases in pulse rate to 3049/s or higher produced uniform magnitudes of sequential EAPs after the first millisecond of stimulation. A large EAP is elicited by the first pulse, followed by a transient depression in excitability, and then by uniform response amplitudes 902. The transient depression in excitability may be caused by the refractory period. The uniform response result corresponds with the ANF model simulation results shown in FIG. 4. The constant response amplitude after 1 ms in FIG. 9 is likely caused by a different, possibly equal sized, pool of fibers responding to each pulse. The constant response amplitude is likely the EAP manifestation of stochastic independence at the single-unit level demonstrated by the ANF model simulations.

If pseudospontaneous activity can be created by a driving signal according to the first preferred embodiment such as high-rate constant pulse train, the auditory nerve can be desynchronized using such a stimulus. Desynchronization of the auditory nerve has various benefits. For example, desynchronization can improve temporal representation of a modulated stimulus. Further, desynchronized auditory nerve responses are a closer match to responses detected in the normal, synaptically driven nerve.

Figure 10:
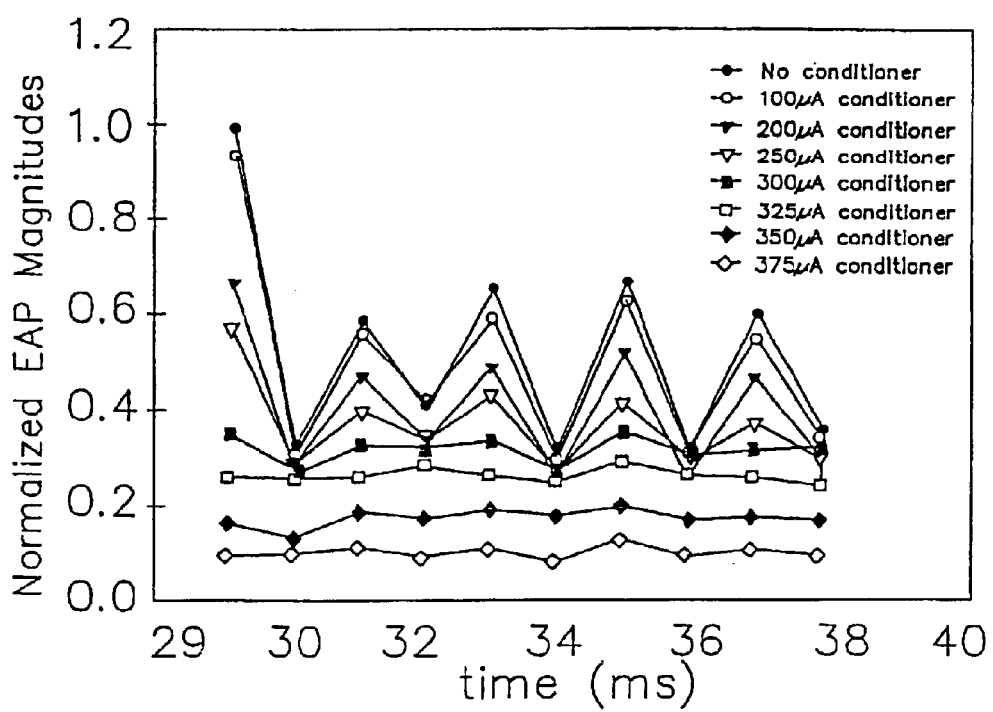
FIG. 10 is a diagram showing magnitudes of EAPs produced with stimulation of implant subject intracochlear electrode with various combinations of conditioner and stimulus.
Figure 11:
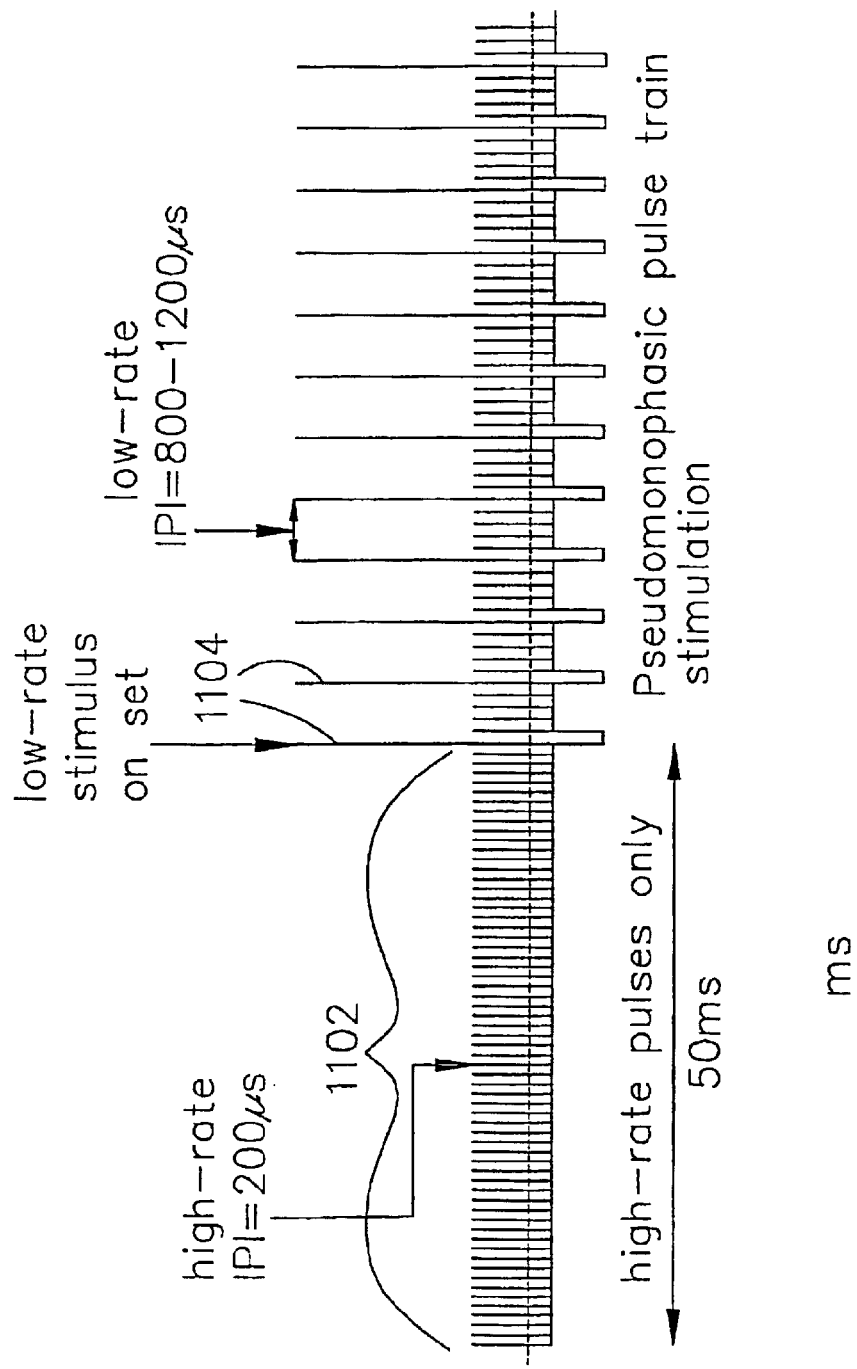
FIG. 11 is a diagram showing a preferred embodiment of a driving signal for an auditory nerve according to the present invention.

FIG. 10 shows desynchronization of an auditory nerve. As shown in FIG. 10 a high rate conditioner (e.g., driving signal) was combined with a low rate stimulus. The conditioner starts at time zero and includes identical pulses presented at the rate of 5039/s. The stimulus starts 29 ms after the onset of the conditioner and includes identical pulses presented at the rate of 1016/s. The amplitude of the stimulus pulses in FIG. 10 were 375 $\mu$A, as in FIG. 8. The amplitude of the conditioner was varied between a 100 $\mu$A conditioner and a 375 $\mu$A conditioner. As shown, EAP magnitudes for the stimulus are normalized to the magnitude of the EAP following the first pulse of the stimulus for the "no conditioner" case. EAPs following the pulses of the stimulus were derived using the subtraction technique similar to FIG. 9. In other words, recording conditions were identical for FIGS. 9–10. FIG. 11 shows an exemplary waveform of a conditioner 1102 and a stimulus 1104.

Thus, increases in the conditioner amplitude from about 200 $\mu$A to 300 $\mu$A produced substantial changes in the pattern of responses to the stimulus. In particular, responses become more uniform with increases in conditioner amplitude over this range. Further, increases in conditioner or driving signal amplitude produced decrements in the magnitude of the EAPs, but do not change the uniform pattern of responses across pulses. The neural representation of the deterministic stimulus is much improved by the addition of the conditioner for conditioner amplitudes at and above about 250 $\mu$A. High levels of responses to the stimuli are maintained with conditioner amplitudes as high as 325 $\mu$A. Thus, relatively large numbers of neurons can be available for representation of the deterministic stimulus over this range.

As described above, driving a population of simulated auditory nerve fibers with high rate pulses according to the first preferred embodiment produces independent spike trains in each simulated fiber after about 20 ms. This pseudospontaneous activity is consistent with a renewal process and yields statistical data comparable to true spontaneous activity within computational limitations. However, the first preferred embodiment of the invention is not intended to be limited to the above. For example, broadband additive noise (e.g., because of rapid signal amplitude transitions) could also evoke pseudospontaneous activity similar to that induced by the high rate pulse train. Any signal that results in pseudospontaneous activity that meets the same tests of independence as true spontaneous activity can be used as the driving signal.

As alluded to hereinabove, in a normal cochlea the inner hair cell-spiral ganglion is inherently "noisy" (i.e., there is a high background of activity in the absence of sound) resulting in spontaneous activity in the auditory nerve. Further, sound produces a slowly progressive response within and across fiber synchronization as intensity is increased. Deficiencies in the perception of sounds by a patient having a defective cochlea fitted with a cochlear implant and receives electrical stimulation using a conventional or prior art speech processing system may be explained, at least in part, by the absence of spontaneous neural activation of the auditory nerve.

In a second preferred embodiment of an inner ear implant according to the present invention, a conditioner or driving signal and a speech signal are provided by the implant. Thus, the induction of pseudospontaneous activation of the auditory nerve by the delivery of a high rate pulse train can be integrated with a speech processing strategy such that the high rate pulse train is superimposed on the speech signal, or added to the speech signal, etc. Desynchronizing the auditory nerve by means of a high rate pulse train, for example, improves the nerve's representation of the temporal details of a speech processor signal, while characteristics of normal hearing such as wide dynamic range both within and across auditory neurons can be restored. These features compensate for deficiencies noted herein above for cochlear implants/speech processing systems of the related art.

Figure 12:
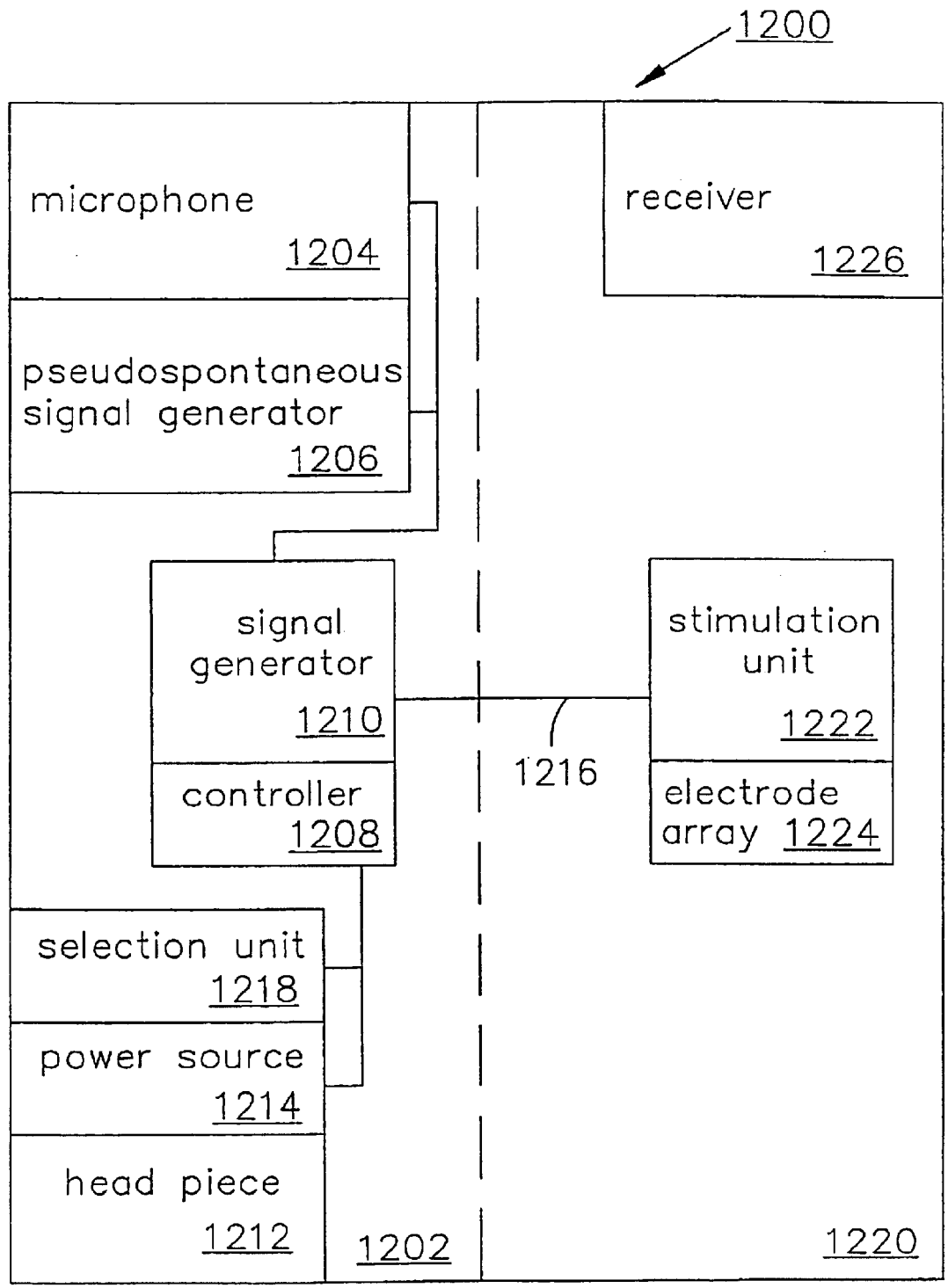
FIG. 12 is a diagram showing a preferred embodiment of an inner ear stimulation system according to the present invention.

As shown in FIG. 12, the second preferred embodiment includes an inner ear stimulation system 1200 that directly electrically stimulates the auditory nerve (not shown). The inner ear stimulation system 1200 can include two components: (1) a wearable or external system, and (2) an implantable system.

An external system 1202 includes a signal generator 1210, a microphone 1204 and a pseudospontaneous signal generator 1206. The signal generator 1210 can include a battery, or an additional equivalent power source 1214, and further includes electronic circuitry, typically including a controller 1208 that controls the signal generator 1210 to produce prescribed electrical signals 1216. The signal generator 1210 not only produces the electrical signals 1216 to electrically simulate speech but also to generate pseudospontaneous activity in the auditory nerve.

The signal generator 1210 combines a driving signal from the pseudospontaneous signal generator 1206 and a signal that represents sound received from the microphone 1204 or the like. Preferably, the signal generator adds the signals from the pseudospontaneous signal generator 1206 and the microphone 1204. The pseudospontaneous signal generator 1206 can produce a driving signal in accordance with the first preferred embodiment. The pseudospontaneous signal generator 1206 can be a signal generator. However, any device that produces a waveform that generates pseudospontaneous activity can be used. That is, any device that produces a pseudospontaneous driving signal. For example, an application program operating on a special purpose computer or microcomputer combined with an A/D converter, a LC resonating circuit, firmware or the like can be used, depending on the exact form of the pseudospontaneous driving signal.

The inner ear stimulation system 1200 provides an improved hearing response to the signal from the microphone 1204 that represents sound. The signal generator 1210 can further vary parameters such as the frequency, amplitude and pulse width of the electrical signals 1216. The external system 1202 can be coupled to a head piece 1212. For example, the head piece 1212 can be an ear piece worn like a hearing aid. Alternatively, the external system 1202 can be a separate unit.

The controller 1208 is preferably implemented on a microprocessor. However, the controller 1208 can also be implemented on a special purpose computer, microcontroller and peripheral integrated circuit elements, an ASIC or other integrated circuit, a hardwired electronic or logic circuit such as a discrete element circuit, a programmable logic device such as a PLD, PLA, FGPA or PAL, or the like. In general, any device on which a finite state machine capable of controlling a signal generator and implementing the flowchart shown in FIG. 14 can be used to implement the controller 1208.

As shown in FIG. 12, an implantable system 1220 of the inner ear stimulation system 1200 can include a stimulator unit 1222 directly coupled to the auditory nerve via implementation in the cochlea (not shown). For example, the stimulator unit 1222 can include an electrode array 1224 or the like implanted into the cochlea of a patient. The electrode array 1224 can be a single electrode or multiple electrodes that stimulate different sites at discrete locations within along the cochlea to evoke nerve activity normally originating from the respective discrete locations. In addition, the implantable system 1220 can be directly or indirectly coupled to the external system 1202.

If indirectly coupled to the external system 1202, the stimulator 1222 can include a receiver 1226. The receiver 1226 can receive information and power from corresponding elements in the external system 1202 through a receiving coil (not shown) attached to the receiver 1226. The power, and data as to which electrode to stimulate, and with what intensity, can be transmitted across the skin using an inductive link from the external signal generator 1210. For example, the receiver 1226 can then provide the signals 1216 to the electrode array 1224. Alternatively, the stimulation unit 1222 can be directly coupled to the external system 1202 via a conductive medium or the like.

Upon installation and periodically thereafter, the patient's hearing based on the electrical signals 1216 can be subsequently monitored or tested. The results of these tests could be used to modify the electrical signal 1216 or select from a plurality of pseudospontaneous driving signals using a selection unit 1218.

The stimulation unit 1222 can operate in multiple modes such as, the "multipolar" or "common ground" stimulation, and "bipolar" stimulation modes. However, the present invention is not intended to be limited to the above. For example, a multipolar or distributed ground system could be used, wherein all other electrodes do not act as a distributed ground, and any electrode could be selected at any time to be a current source, a current sink, or to be inactive during either stimulation phase with suitable modification of the receiver-stimulator. Thus, there can be flexibility in the choice of a stimulation strategy by the stimulation unit 1222 to provide the electrical signals 1216 to the auditory nerve. However, the specific method or combination of electrodes in the electrode array 1224 used to apply the driving signal must result in the pseudospontaneous activity being generated and a signal representing sound being provided. The present invention is not intended to be limited to a specific design of the electrode array 1224, but rather a number of alternative electrode designs as have been described in the prior art could be used.

Figure 13A:
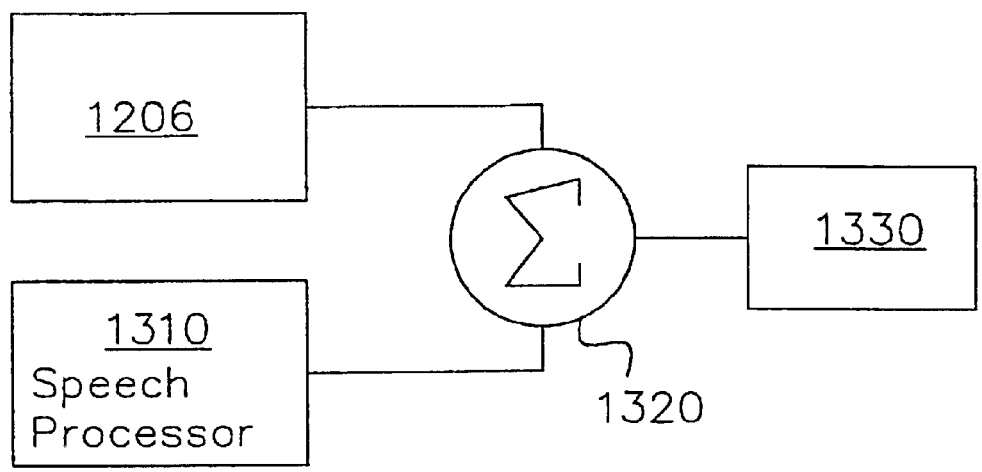
FIGS. 13A and 13B are diagrams showing exemplary implementations of the inner ear stimulation system of FIG. 12.
Figure 13B:
Figure 13B:

FIGS. 13A and 13B show exemplary implementations of the inner ear stimulation system 1200. The pseudospontaneous signal generator 1206 driving signal is combined with a signal from a speech processor 1310. The rate of the speech processing signal is less than the rate of the driving signal. A number of alternative speech processor designs as have been described in the prior art can be used. As shown in FIG. 13A, the speech signal is preferably added to the driving signal in a combining circuit 1320. However, the signals can be superimposed or modulated together in the combining circuit 1320. A combined signal is then transmitted to a electrode 1330 of an electrode array (not shown). FIG. 13B shows the speech signal and the driving signal being delivered separately to the auditory nerve (not shown) using the inner ear stimulation system 1200. Electrodes 1330 and 1330 represent individual electrodes or electrode subsets in an electrode array.

Figure 14:
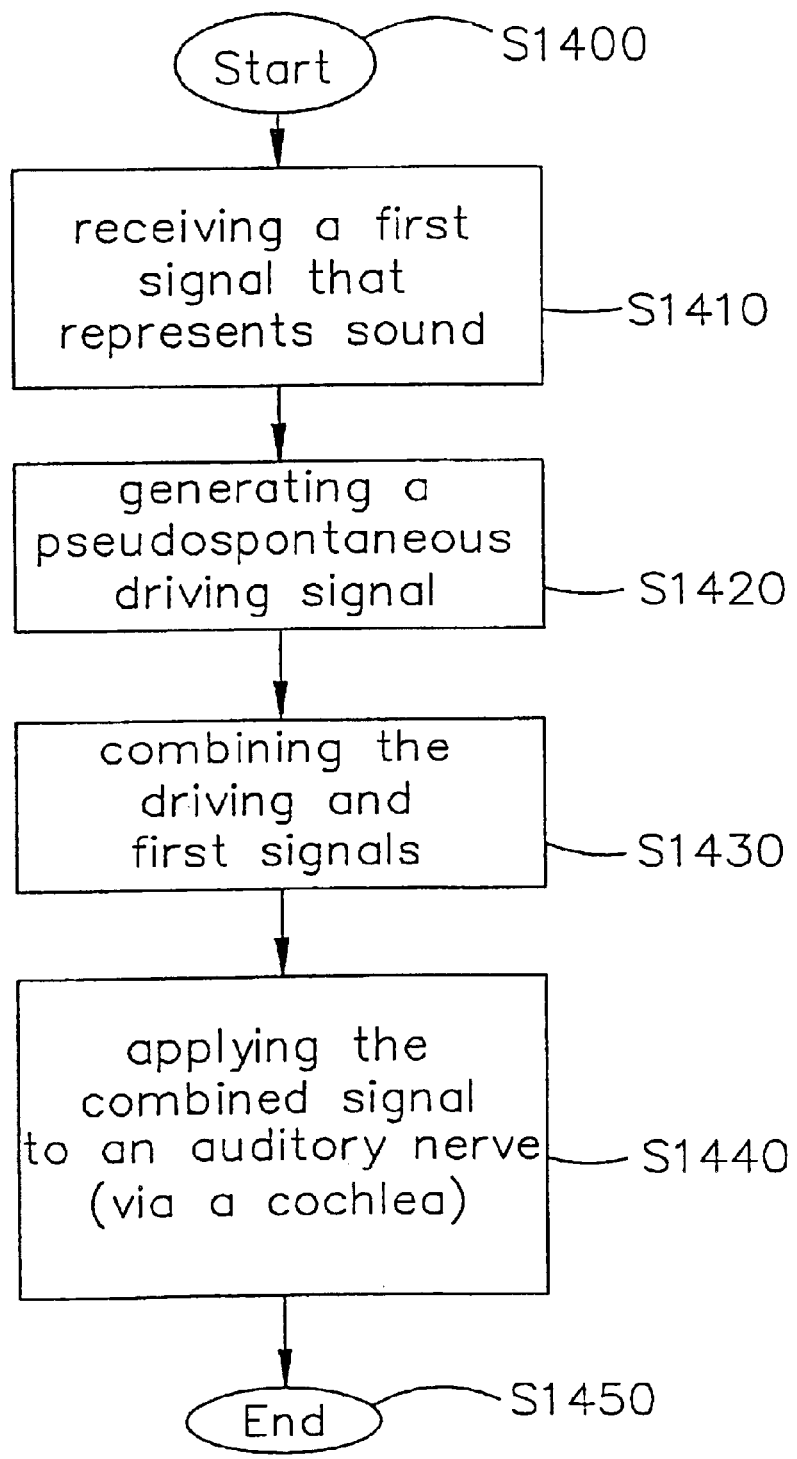
FIG. 14 is a flowchart showing of a preferred embodiment of a method for speech processing using pseudospontaneous stimulation of the auditory nerve.
Figure 15:
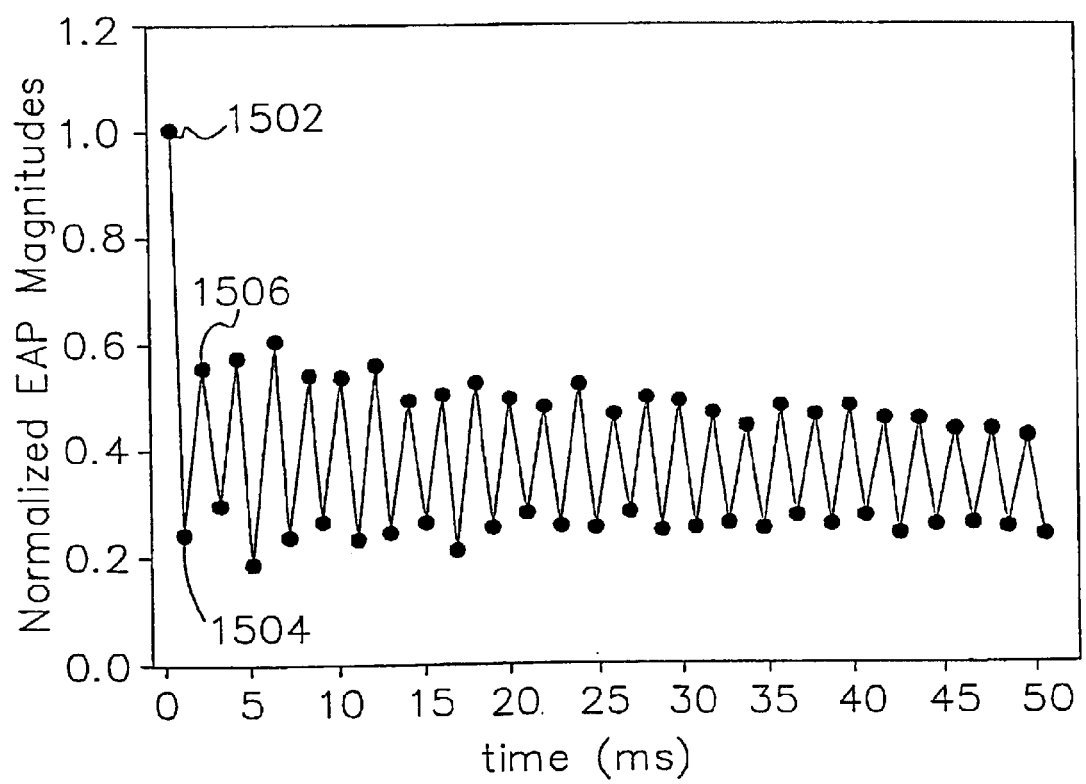
FIG. 15 is a diagram showing related art EAP N1P1 magnitudes from a human subjected to a stimulus.

A third preferred embodiment of a method for speech processing using pseudospontaneous stimulation according to the present invention will now be described. As shown in FIG. 14, the process starts in step S1400. From step S1400, control continues to step S1410. In step S1410, a signal representing sound is received. For example, the signal could be individually generated or generated from a combination of a microphone, prerecordings, or input from a plurality of sources (e.g., a television, etc.). From step S1410, control continues to step S1420.

In step S1420, a pseudospontaneous driving signal is generated. For example, a driving signal according to the first preferred embodiment can be generated or selected in step S1420. From step S1420, control continues to step S1430. In step S1430, the driving signal and the first signal are combined. From step S1430, control continues to step S1440.

In step S1440, the combined signal is applied to the auditory nerve. For example, an inner ear implant according to the second preferred embodiment can be used to implement a method according to the third preferred embodiment. Because of the pseudospontaneous activity generated in the auditory nerve by the driving signal, the response of the auditory nerve to the signal representing sound is improved. Even with a broad range of electrical thresholds in the auditory nerve (approximately 12 dB), near physiologic rates may be maintained across most of the auditory nerve with multiple electrodes. From step S1440, control continues to step S1450 where the process is completed. The method according to the third preferred embodiment can optionally include a feed-back test loop to modify or merely select one of a plurality of selectable pseudospontaneous driving signals based on a subset of parameters specifically designed and determined for an individual patient.

As described above, the preferred embodiments according to the present invention have various advantages. The preferred embodiments generate stochastically independent or pseudospontaneous neural activity, for example, in an auditory nerve to improve a speech processing apparatus and method. Further, the stimulus that evokes pseudospontaneous activity should not be perceptible over the long term as long as the rate is physiologic. According to the preferred embodiments, a conditioner signal and a data signal can be combined and the combined signal is provided to a neural system to improve the response of the neural system to the data signal. For example, an inner ear implant such as a cochlear implant, according to the preferred embodiments generates pseudospontaneous activity in an auditory nerve, which improves a response to signals representing sound.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A cochlear system, comprising:
a signal generator that generates a second signal capable of causing pseudospontaneous activity in an auditory nerve;
a signal processor that combines a first signal that represents sound and the second signal to output a combined signal; and
a stimulation unit coupled to the signal processor that receives the combined signal from the signal processor, wherein the stimulation unit is configured to apply the combined signal to the auditory nerve.

2. The system according to claim 1, wherein the stimulation unit is an electrode array unit that is coupled to the auditory nerve.

3. The system according to claim 2, wherein the first signal is applied to a first subset of electrodes in the electrode array and the second signal is applied to a second subset of electrodes in the electrode array.

4. The system according to claim 1, wherein the second signal includes one of (i) a pulse train generating substantially continuous pseudospontaneous activity, (ii) a broad band noise, and (iii) at least fluctuations in amplitude greater than prescribed amount at a frequency above approximately 2 k Hz that causes statistically independent activity in a plurality of nerve fibers of the nerve.

5. The system according to claim 1, wherein the pseudospontaneous activity is demonstrated by statistically independent activity in a plurality of nerve fibers in the auditory nerve.

6. The system according to claim 1, wherein the second signal includes rapid state transitions and a frequency greater than approximately 3 kilohertz.

7. The system according to claim 1, wherein the signal processor determines the combined signal by summing the first and second signals.

8. The system according to claim 1, further comprising a microphone that generates the first signal, wherein the microphone is coupled to the signal processor.

9. The system according to claim 1, wherein the signal processor further comprises a combining circuit that logically processes the first and second signals, wherein the combining circuit ANDs the first and second signals.

10. The system according to claim 1, wherein a microphone, the signal processor and the signal generator are positioned external to an ear, wherein the stimulation unit is coupled by a wire to the signal processor, and wherein the stimulation unit is coupled to the auditory nerve via a cochlea.

11. A method for generating a driving signal for an auditory implant, comprising:
receiving a first signal;
generating a second signal that causes pseudospontaneous activity in an acoustic nerve;
combining the first and second signals to generate the driving signal; and
applying the combined signal to the acoustic nerve.

12. The method according to claim 11, wherein the first signal represents at least one of speech, emergency signals and control information.

13. The method according to claim 11, wherein the combining step performs at least one of summing and multiplying the first and second signals.

14. The method of claim 11, wherein the applying the combined signal generates substantially continuous pseudospontaneous activity.

15. The method of claim 11, wherein the second signal is not continuously applied.

16. The method of claim 11, wherein the second signal includes one of (i) a pulse train generating substantially continuous pseudospontaneous activity, (ii) a broad band noise, and (iii) at least fluctuations in amplitude greater than prescribed amount at a frequency above approximately 2 k Hz that causes statistically independent activity in a plurality of nerve fibers of the nerve, wherein the driving signal is used to modulate a carrier signal.

17. An auditory prosthesis for receiving an auditory signal representing sound and supplying an electrical signal which is adapted to stimulate the auditory nerve of a person, comprising:

pseudospontaneous generation means for generating a pseudospontaneous driving signal;

transducer means adapted to receive the auditory signal and the pseudospontaneous driving signal for transforming the auditory signal and the pseudospontaneous driving signal to electrical input signals; and stimulation means, operatively coupled to the electrical input signals generated by the transducer means, for stimulating the auditory nerve at defined locations within the cochlea, wherein at least one of the plurality of electrical signals is configured to cause statistically independent activity in a plurality of nerve fibers of an auditory nerve.

18. The auditory prosthesis of claim 17, wherein the transducer means further performs at least one of the summing and multiplying the auditory signal and the pseudospontaneous driving signal.

19. The auditory prosthesis of claim 17, wherein the pseudospontaneous driving signal includes one of (i) a pulse train generating substantially continuous activation, (ii) a broad band noise, or (iii) at least fluctuations in amplitude greater than prescribed amount at a frequency above approximately 2 k Hz, wherein the electrical signals stimulate the auditory nerve.

20. A neural prosthetic apparatus, comprising.

a signal generator that generates a second signal;

a signal processor that combines a first signal that represents sound and the second signal to output a combined signal, wherein a carrier signal is modulated with the combined signal; and stimulation unit coupled to the signal processor that receives and demodulates the carrier signal to obtain the combined signal from the signal processor for application to the auditory nerve, wherein the second signal includes at least fluctuations in amplitude greater than a prescribed amount at a frequency above approximately 2 kHz.

21. The apparatus according to claim 20, wherein the stimulation unit is an electrode array unit that is coupled to the auditory nerve, and wherein the first signal is applied to a first subset of electrodes in the electrode array and the second signal is applied to a second subset of electrodes in the electrode array.

22. The apparatus according to claim 20, wherein the second signal generates statistically independent activity in a plurality of nerve fibers in the auditory nerve.

23. The apparatus according to claim 20, wherein the auditory nerve comprises a plurality of nerve fibers, and wherein the second signal comprises one or more signals that generate a substantially maximum firing rate of the plurality of nerve fibers.

24. The apparatus according to claim 20, wherein the second signal includes one of (i) a pulse train generating substantially continuous pseudospontaneous activity being statistically independent activity in a plurality of nerve fibers of the nerve, and (ii) a broad band noise that causes statistically independent activity in the plurality of nerve fibers of the nerve.

25. The apparatus according to claim 20, wherein the prosthesis is a cochlear implant applying current to the auditory nerve, wherein the stimulation unit is configured to apply the combined signal to the auditory nerve.

26. The apparatus according to claim 20, wherein the pseudospontaneous activity continues after the second signal is stopped.

27. A method of modifying a neural prosthetic apparatus that receives an information signal and supplies a corresponding electrical signal to stimulate an auditory nerve, comprising:

providing a pseudospontaneous signal generator that generates a second signal; and providing an electrical coupling means for supporting an electrical connection from the pseudospontaneous signal generator to at least one electrical contact, and wherein the second signal is configured to induce a random pattern of activation in the auditory nerve mimicking the spontaneous neural activity of the auditory nerve.

28. The method of claim 27, wherein the information signal represents at least one of speech, emergency signals and control information, and wherein the second signal includes one of (i) a pulse train generating substantially continuous pseudospontaneous activity, (ii) a broad band noise, (iii) at least fluctuations in amplitude greater than prescribed amount at a frequency above approximately 2 k Hz, and (iv) at least fluctuations in amplitude greater than prescribed amount at a frequency that causes statistically independent activity in a plurality of nerve fibers of the auditory nerve.

29. The method of claim 27, wherein the neural prosthetic apparatus is a cochlear implant, wherein the second signal and the electrical signal are used to modulate a carrier signal.

* * * * *